US012620480B2

(12) United States Patent
Tan

(10) Patent No.: US 12,620,480 B2
(45) Date of Patent: May 5, 2026

(54) APHERESIS DEVICES FLEET MANAGEMENT SYSTEM AND METHOD

(71) Applicant: Haemonetics Corporation, Boston, MA (US)

(72) Inventor: Melvin Tan, Edmonton (CA)

(73) Assignee: Haemonetics Corporation, Boston, MA (US)

( * ) Notice: Subject to any disclaimer, the term of this patent is extended or adjusted under 35 U.S.C. 154(b) by 816 days.

(21) Appl. No.: 17/271,144

(22) PCT Filed: Aug. 26, 2019

(86) PCT No.: PCT/US2019/048092
§ 371 (c)(1),
(2) Date: Feb. 24, 2021

(87) PCT Pub. No.: WO2020/046788
PCT Pub. Date: Mar. 5, 2020

(65) Prior Publication Data
US 2021/0249126 A1     Aug. 12, 2021

Related U.S. Application Data

(60) Provisional application No. 62/722,960, filed on Aug. 26, 2018.

(51) Int. Cl.
*G16H 40/40*          (2018.01)
*G06F 8/65*           (2018.01)
(Continued)

(52) U.S. Cl.
CPC .............. *G16H 40/40* (2018.01); *G06F 8/65* (2013.01); *G06F 8/71* (2013.01); *G16H 10/60* (2018.01); *G16H 50/20* (2018.01)

(58) Field of Classification Search
None
See application file for complete search history.

(56)          References Cited

U.S. PATENT DOCUMENTS

2001/0034614  A1*  10/2001  Fletcher-Haynes .... G16H 20/40
                                                                  705/2
2010/0049542  A1*   2/2010  Benjamin .......... G06Q 10/0637
                                                                 705/28

(Continued)

FOREIGN PATENT DOCUMENTS

JP        2009-53730    A      3/2009
WO        2013/017580   A2     2/2013

OTHER PUBLICATIONS

Andres F. Osorio, Sally C. Brailsford, Honora K. Smith, Whole blood or apheresis donations? A multi-objective stochastic optimization approach, European Journal of Operational Research, vol. 266, Issue 1, Apr. 1, 2018, pp. 193-204, ISSN 0377-2217, https://doi.org/10.1016/j.ejor.2017.09.005. (Year: 2018).*

(Continued)

*Primary Examiner* — Devin C Hein
(74) *Attorney, Agent, or Firm* — McCarter & English, LLP; Jonathan C. Lovely

(57)          ABSTRACT

A fleet management system includes apheresis devices and a fleet management device remotely located from and in communication with the apheresis devices. Each apheresis device has a controller, firmware and firmware settings. The fleet management device includes an interface to allow a user to interact with the fleet management device, a server and a processor. The server receives information regarding the firmware/firmware settings of each of the apheresis devices and a firmware file from the user and/or a remote repository. The processor processes the information to determine which of the apheresis devices requires an update to the firmware/firmware settings. The server then distributes
(Continued)

the firmware file to each apheresis device that requires the update. The system may also develop a fleet model for one or more donation centers that includes a recommend quantity of devices for the location(s) and/or whether devices should be moved from one location to another.

36 Claims, 6 Drawing Sheets

(51)  Int. Cl.
    *G06F 8/71*        (2018.01)
    *G16H 10/60*       (2018.01)
    *G16H 50/20*       (2018.01)

(56)                References Cited

U.S. PATENT DOCUMENTS

| | | | |
|---|---|---|---|
| 2010/0169876 A1 | 7/2010 | Mann | |
| 2012/0096451 A1 | 4/2012 | Tenbarge et al. | |
| 2012/0265099 A1 | 10/2012 | Goodnow, II et al. | |
| 2013/0036210 A1* | 2/2013 | Birtwhistle | G16H 40/40 |
| | | | 709/221 |
| 2013/0104120 A1* | 4/2013 | Arrizza | A61M 5/142 |
| | | | 717/173 |
| 2013/0179871 A1 | 7/2013 | Nagao et al. | |
| 2014/0195254 A1* | 7/2014 | McElroy | G16H 40/20 |
| | | | 705/2 |
| 2014/0278499 A1* | 9/2014 | Bowman | G06Q 30/0601 |
| | | | 705/2 |
| 2015/0172435 A1 | 6/2015 | Choi et al. | |
| 2016/0335414 A1* | 11/2016 | Isaacs | G16H 40/40 |
| 2018/0144817 A1 | 5/2018 | Lofgren et al. | |
| 2020/0027541 A1* | 1/2020 | Xavier | G06F 8/65 |

OTHER PUBLICATIONS

International Search Report and Written Opinion for Application No. PCT/US2019/048092, dated Nov. 8, 2019, 13 pages.

* cited by examiner

100

Apheresis Device Schematic

Apheresis Device
Controller
226

Firmware 420

Firmware Setting
430A

Firmware Setting
430B

Firmware Setting
430C

Apheresis Device

Figure 5:
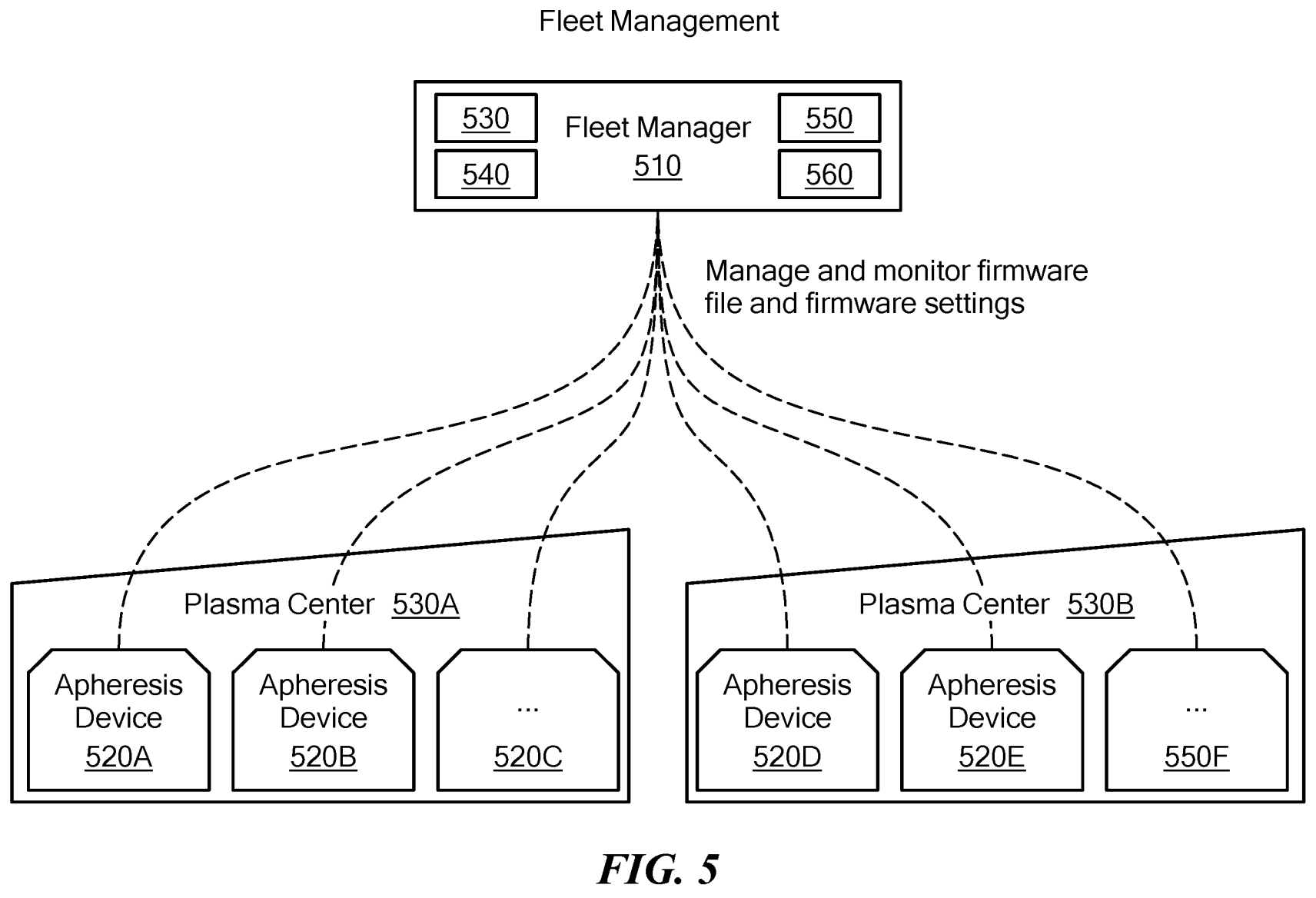

Fleet Management

Fleet Manager
510

550

560

530

540

Manage and monitor firmware
file and firmware settings

Plasma Center　530B

Apheresis
Device
520D

Apheresis
Device
520E

...
550F

Plasma Center　530A

Apheresis
Device
520A

Apheresis
Device
520B

APHERESIS DEVICES FLEET MANAGEMENT SYSTEM AND METHOD

PRIORITY

This patent application is a 35 U.S.C. § 371 national stage filing of International Application No. PCT/US2019/048092, filed on Aug. 26, 2019, which claims priority from U.S. Provisional Application No. 62/722,960, filed Aug. 26, 2018, entitled "Apheresis Devices Fleet Management,", and naming Melvin Tan as inventor. The disclosure of each of the foregoing applications is incorporated herein, in its entirety, by reference.

TECHNICAL FIELD

The present invention relates to managing apheresis devices, and more particularly to the oversight and management of a plurality of apheresis devices from a remote location and methods of the same.

BACKGROUND ART

Apheresis is a procedure in which individual blood components can be separated and collected from whole blood withdrawn from a subject, and an apheresis device is medical equipment designed and intended to perform an apheresis procedure. Donation centers typically have more than one apheresis device and each device is usually configured to operate in exactly the same way to comply with the donation center's standard operating procedures and for regulatory compliance. The configuration of the apheresis device is predicated by both the embedded software in the device, also known as the device firmware, and the varied collection of firmware settings to dictate how each feature of the device operates and performs.

To change or update the firmware version of an apheresis device, the user currently has to locally access the device through the device's built-in controller, input methods, and display outputs. Then the user downloads the firmware file to the individual device and performs the firmware update from within the built-in device controller (i.e., at each device). To perform the same procedure on a number of apheresis devices, the above procedure must be repeated for each of the devices locally.

Similarly, to change or update a firmware setting value of an apheresis device, the user must also locally accesses the device through the device's built-in controller, input methods, and display outputs. This, in turn, gives the user access to the firmware settings and allows the user to change the firmware setting value(s) by manual manipulation or by reading, inputting, or scanning a pre-encoded firmware setting. To perform the same procedure on a plurality of apheresis devices, the user must once again repeat the procedure for each of the devices locally.

In addition to having to update each device individually, the user must also access each device locally to merely inspect whether the devices are configured to run exactly the same way. Therefore, after the user accesses the apheresis device through the device's built-in controller, input methods, and display outputs, the user may check the firmware version and firmware setting values for individual devices. This is performed individually on each device by physically manipulating the controls of the apheresis device and reviewing the values of each firmware setting. Depending on the number of devices within a given donation center, this may be a very time consuming task.

SUMMARY OF THE EMBODIMENTS

In various embodiments of the present invention, a company staff member may use a computer system from a remote location to oversee and manage at least one apheresis device in the company's fleet. From this remote location, the user can manage the apheresis device firmware file, firmware settings, and perform inspection of firmware settings without requiring any physical manipulation of the controls on the built-in apheresis device controller itself. The system may be connected from a central location or a remote location to a number of apheresis devices. This connectivity may be persistent or may be intermittent.

The system may receive a firmware file from the user or from an external repository, and the file may be distributed to at least one apheresis device for installation on the device. The system may alert the user when the firmware file has been installed successfully or unsuccessfully. Alternatively, the user may also use the system to inspect the firmware version of the apheresis device to confirm if the firmware file has been installed successfully or unsuccessfully.

The system may receive a firmware setting file from the user, from an external repository, or from an apheresis device. The firmware setting file may be used for configuring a number of apheresis devices in the company's fleet (e.g., within one donation center or multiple donation centers). The firmware setting file may be distributed to the apheresis device(s) for the device to apply the changes represented in the firmware setting file. The system may alert the user when the firmware setting changes have been applied successfully or unsuccessfully. Alternatively, the user may also use the system to inspect the firmware settings of the apheresis device to confirm if the firmware setting file changes were applied successfully or unsuccessfully.

In some embodiments, the system may use the connectivity to the apheresis devices in the fleet to collect information about the firmware version or the firmware setting values from the individual devices in the fleet. The system may then aggregate, combine, and analyze the information to determine if there are any differences in the firmware version or firmware setting values between apheresis devices. The system may also create a notification, for example, an e-mail to a user, when it detects a firmware version or firmware setting discrepancy.

In further embodiments, the system may use heuristics based on the location of apheresis devices in the fleet and the productivity information from those locations to create a fleet model. Fleet modeling may determine the optimal number of devices for a location's profile and may provide a directive for the user to either add or remove devices from the location. The system may use information based on productivity, utilization, telemetry, inventory, quantity, consumption, cost, timing, average, rate, speed data and/or other performance or production data of the same to determine the optimal fleet model for the various locations. The system may also use the apheresis device location data to determine plasma center locations that will require changes to device placement to meet the requirements of the new fleet model and, perhaps, provide a directive to the user in the form of digital assistance with instructions to adjust placement of apheresis devices at specific plasma center locations in the company.

Additionally or alternatively, the system may use the connectivity to the apheresis devices in the fleet to monitor for firmware version differences or firmware settings differences. Unanticipated differences amongst apheresis devices (i.e., mutations) may be tracked, logged, and reported to the company user or user of the same. Alternatively, the system may self-correct any mutations between apheresis devices by sending a firmware file of firmware settings file to be updated on the non-conforming apheresis devices.

In accordance with further embodiments, a fleet management system includes a first plurality of apheresis devices and a fleet management device. Each of the apheresis devices may have a controller, firmware and firmware settings. The fleet management device may be remotely located from and in communication with each of the apheresis devices. The fleet management device may include an interface, a server and a processor. The interface may allow a user to interact with the fleet management device and the server may receive information regarding the firmware and firmware settings from each of the apheresis devices and may receive a firmware file from the user and/or a remote repository. The processor may process the information received from the apheresis devices to determine which of the apheresis devices requires an update to the firmware and/or firmware settings. The server may then distribute the firmware file to each of the apheresis devices that require the update.

The fleet management system may also include a second plurality of apheresis devices that are located remotely from and in communication with the fleet management device. The server may also receive information regarding the firmware and firmware settings from each of the second plurality of apheresis devices, and the processor may process the information to determine which of these apheresis devices require an update to the firmware and/or firmware settings. The server may then distribute the firmware file to each of the devices that require the update. The first plurality of apheresis devices may be located in a first donation center and the second plurality of apheresis devices may be located in a second donation center.

In other embodiments, the fleet management device may allow a user to remotely manage the firmware files and/or firmware settings of each of the apheresis devices. For example, the fleet management device may alert a user if the firmware file and/or a firmware setting file is successfully or unsuccessfully installed on the apheresis devices. The fleet management device may also collect additional information from each of the apheresis devices such as data related to the apheresis procedures performed, productivity information, utilization information, quantity of apheresis devices within a donation center, performance data, and/or inventory data. The processor may analyze the information regarding the firmware and firmware settings (or other information) of each of the apheresis devices to determine if there is a discrepancy in a firmware version or firmware setting value of each of the apheresis devices. In such embodiments, the fleet management device may notify the user of the discrepancy.

In additional embodiments, the fleet management device may generate a fleet model for one or more donation centers. For example, the fleet model may be based, at least in part, upon information regarding productivity, utilization, telemetry, inventory, quantity, consumption, cost, timing, average, rate, speed data and other performance or production data of the same. The fleet model may include recommended apheresis device changes for one or more donation centers and the server may notify the user of the fleet model and recommended apheresis device changes. The fleet management device may also include a data storage device that stores information received from the apheresis device.

In accordance with further embodiments, a fleet management device may include an interface that allows a user to interact with the fleet management device and a server in communication with a first plurality of apheresis devices. The apheresis devices may be located remotely from the fleet management device, and the server may receive information regarding the firmware and firmware settings from each of the apheresis devices and receive a firmware file from the user and/or a remote repository. A processor may process the information received from each of the apheresis devices to determine which of the apheresis devices requires an update to the firmware and/or firmware settings. The server may then distribute the firmware file to each of the apheresis devices that require the update.

The server may also be in communication with a second plurality of apheresis devices that are located remotely from the fleet management device. In such embodiments, the server may also receive information regarding the firmware and firmware settings from each of the second plurality of apheresis devices and the processor may process the information received to determine which of the apheresis devices requires the update. The server may then distribute the firmware file to each of the second plurality of apheresis devices that require the update.

The fleet management device may allow a user to remotely manage and/or monitor the firmware files and/or firmware settings of each of the first plurality of apheresis devices and the server may alert the user if the firmware file and/or a firmware setting file is successfully or unsuccessfully installed. Additionally or alternatively, the server may receive additional information (e.g., the apheresis procedures performed, productivity information, utilization information, quantity of apheresis devices within a donation center, performance data, and inventory data) from each of the first plurality of apheresis devices.

In some embodiments, the processor may determine if there is a discrepancy in a firmware version or firmware setting values for the apheresis devices by analyzing the information regarding the firmware and firmware settings of each of the apheresis devices. The server may notify the user of any discrepancy. Additionally or alternatively, the server and/or the processor may generate a fleet model for one or more donation centers. The fleet model may be based on information regarding productivity, utilization, telemetry, inventory, quantity, consumption, cost, timing, average, rate, speed data and other performance or production data of the same. The fleet model may include recommended apheresis device changes for one or more donation centers, and the server may notify the user of the fleet model and recommended apheresis device changes. The device changes may include the quantity of devices that should be within a given donation center, the location of the device, and whether one or more of the devices should be moved from one center to a different center.

In accordance with still further embodiments, a method for managing a fleet of apheresis devices includes remotely connecting to a first plurality of apheresis devices, and receiving, in a server of a fleet management device, (1) information regarding the firmware and firmware settings of each of the first plurality of apheresis devices (e.g., from the apheresis devices), and (2) a firmware file (e.g., from a user and/or a remote repository). The method may then process, in a processor of the fleet management device, the information received from the apheresis devices to determine which of the apheresis devices requires an update to the firmware and/or firmware settings. The method may then distribute, using the server of the fleet management device, the firmware file to each of the first plurality of apheresis devices that require the update.

In some embodiments, the method may also include connecting to a second plurality of apheresis devices located remotely from the fleet management device and receiving, in the server of the fleet management device, information regarding the firmware and firmware settings of each of the second plurality of apheresis devices. The method may then (1) process, using the processor of the fleet management device, the information received from each of the second plurality of apheresis devices to determine which of the second plurality of apheresis devices requires an update to the firmware and/or firmware settings, and (2) distribute, using the server of the fleet management device, the firmware file to each of the second plurality of apheresis devices that require the update.

Additionally, the method may manage and/or monitor, using the fleet management device, the firmware files and/or firmware settings of each of the first plurality of apheresis devices and/or generate an alert to a user if the firmware file and/or a firmware setting file is successfully or unsuccessfully installed on the apheresis devices. The method may also collect and store (e.g., within a data storage device) additional information from each of the first plurality of apheresis devices. For example, the method may collect information regarding the apheresis procedures performed, productivity information, utilization information, quantity of apheresis devices within a donation center, performance data, and inventory data. The method may also analyze, using the processor, the information regarding the firmware and firmware settings of each of the apheresis devices to determine if there is a discrepancy in a firmware version or firmware setting value of each of the apheresis devices. If there is a discrepancy, the method may notify the user of the discrepancy.

In additional embodiments, the method may generate a fleet model for one or more donation centers. The fleet model may be based, at least in part, upon information related to productivity, utilization, telemetry, inventory, quantity, consumption, cost, timing, average, rate, speed data and other performance or production data of the same. The fleet model may include recommended apheresis device changes for one or more donation centers, and the method may notify the user of the fleet model and recommended apheresis device changes. The method may also store, in a data storage device in the fleet management device, information received from the apheresis devices.

BRIEF DESCRIPTION OF THE DRAWINGS

The foregoing features of embodiments will be more readily understood by reference to the following detailed description, taken with reference to the accompanying drawings, in which:

FIG. 5 schematically shows a fleet management providing oversight to a plurality of apheresis devices at a plurality of plasma center locations, in accordance with some embodiments of the present invention.

DETAILED DESCRIPTION OF SPECIFIC EMBODIMENTS

In illustrative embodiments, a fleet management system has a fleet management device that is located remotely from and in communication with several apheresis devices. The fleet management device may receive information regarding the firmware and firmware settings from each of the first plurality of apheresis devices and a firmware file. The device may then process the information to determine which of the apheresis devices require an update, and then distribute the firmware file to each of the apheresis devices that require the update, for example, to ensure that each of the apheresis devices have the same firmware and firmware settings.

Figure 1:
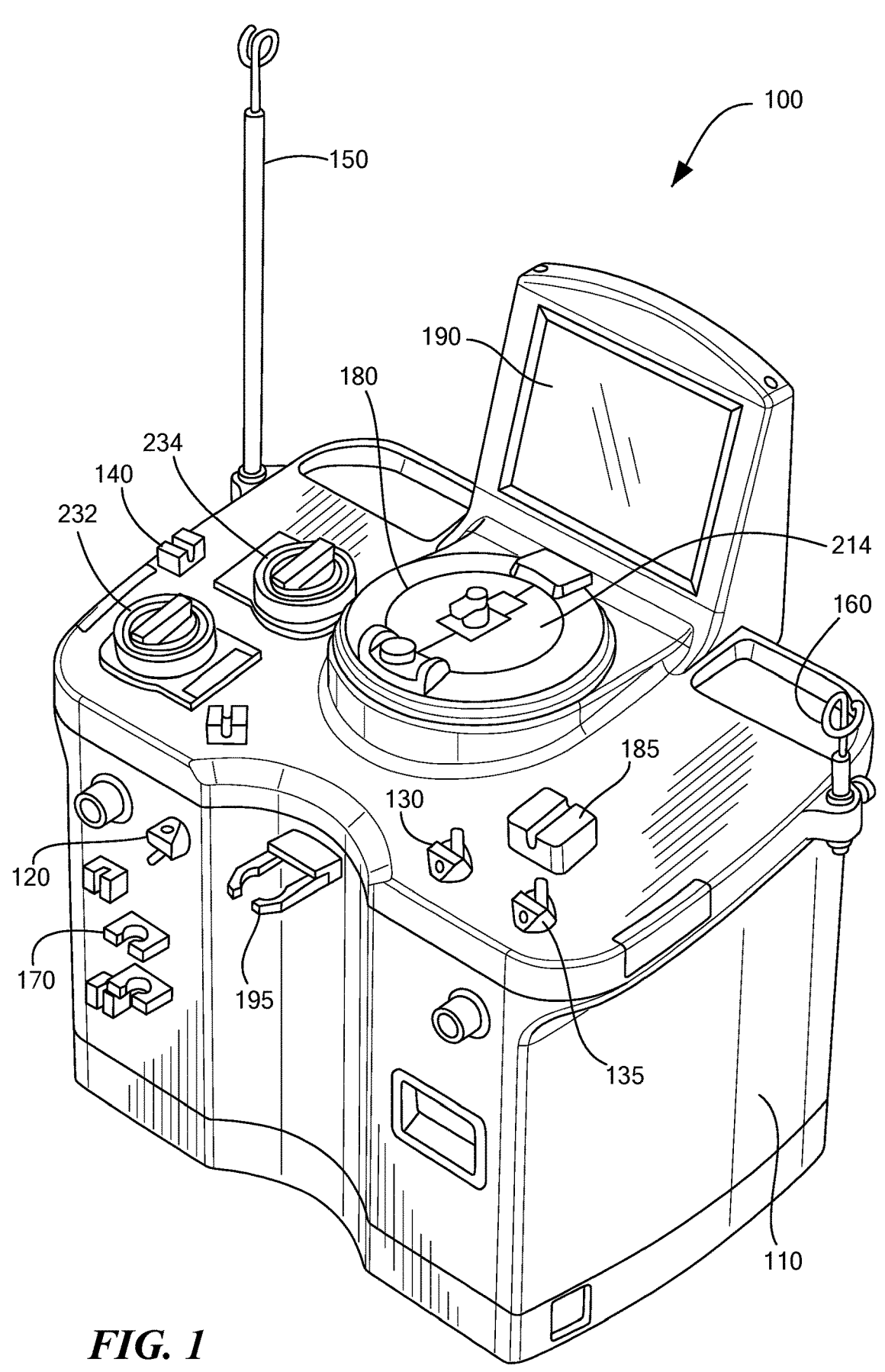
FIG. 1 schematically shows a perspective view of a blood processing system in accordance with some embodiments of the present invention.
Figure 2:
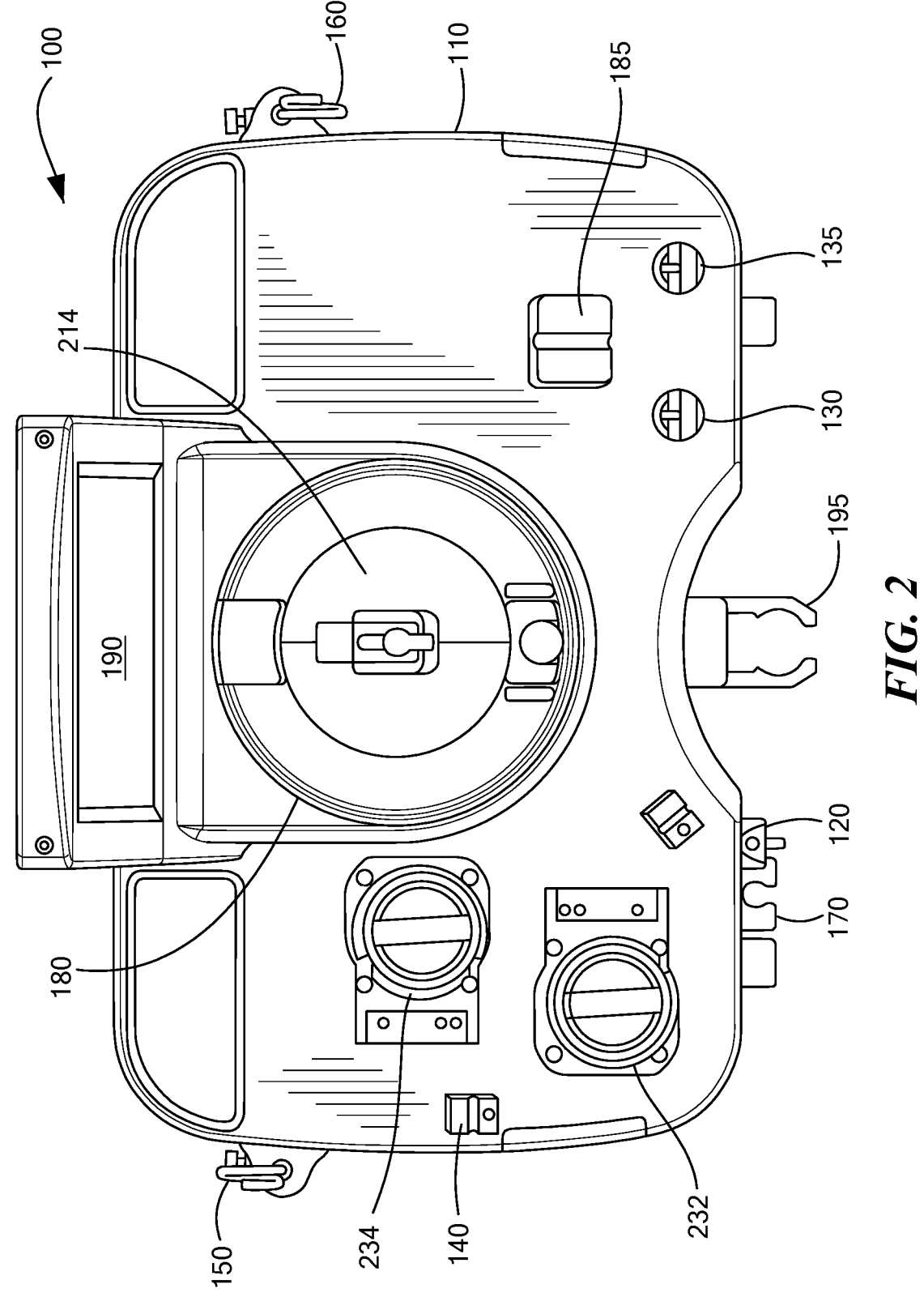
FIG. 2 schematically shows a top view of the blood processing system of FIG. 1, in accordance with some embodiments of the present invention.
Figure 3:
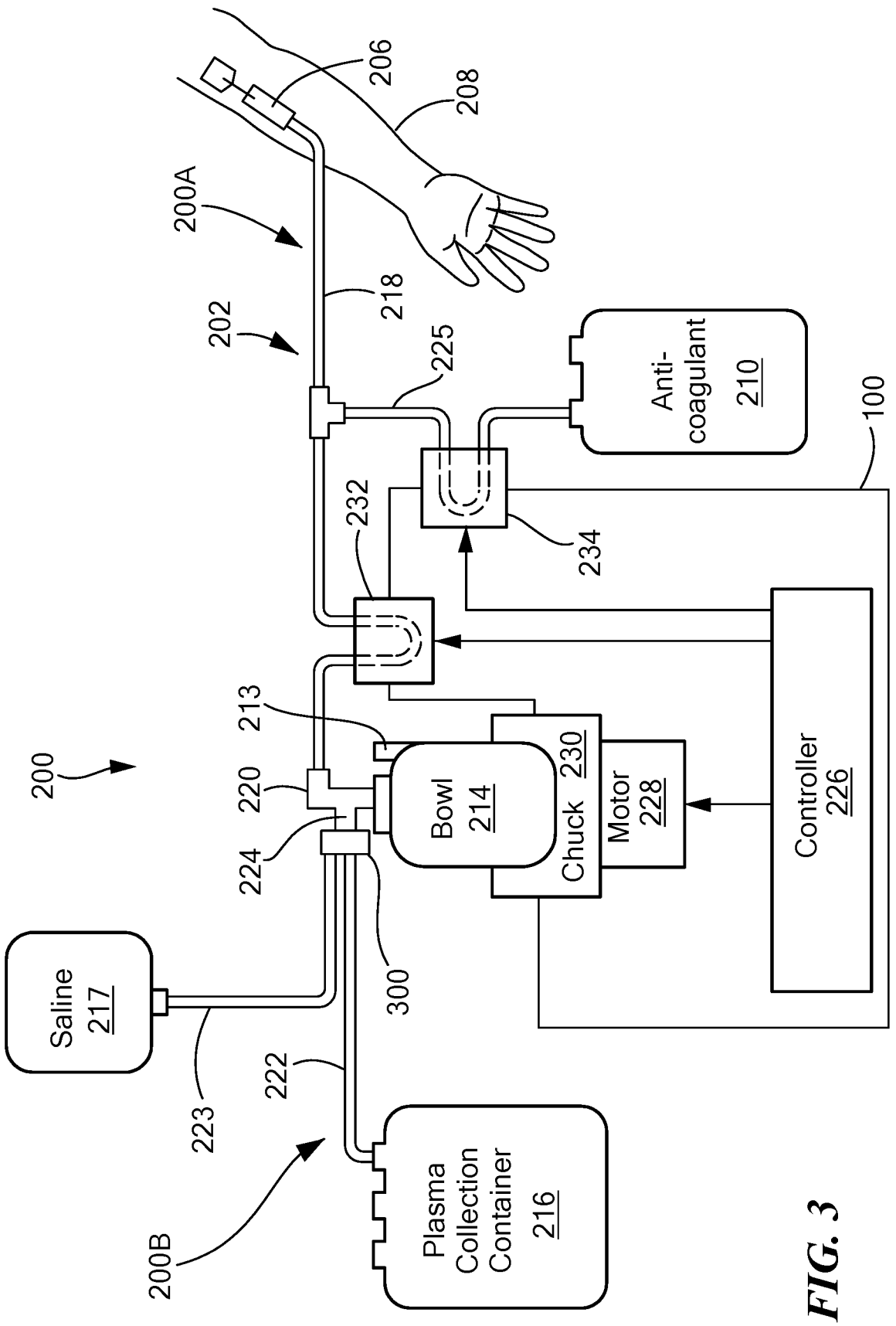
FIG. 3 schematically shows a disposable set installed within the blood processing system of FIG. 1, in accordance with some embodiments of the present invention.

As shown in FIGS. 1 and 2, the blood processing system 100 includes a cabinet 110 that houses the main components of the system 100 (e.g., the non-disposable components). Within the cabinet 110, the system 100 may include a first/blood pump 232 that draws whole blood from a subject, and a second/anticoagulant pump 234 that pumps anticoagulant through the system 100 and into the drawn whole blood. Additionally, the system 100 may include a number of valves that may be opened and/or closed to control the fluid flow through the system 100. For example, the system 100 may include a donor valve 120 that may open and close to selectively prevent and allow fluid flow through a donor line 218 (e.g., an inlet line; FIG. 3), and a plasma valve 130 that selectively prevents and allows fluid flow through an outlet/plasma line 222 (FIG. 3). Some embodiments may also include a saline valve 135 that selectively prevents and allows saline to flow through a saline line 223.

To facilitate the connection and installation of a disposable set and to support the corresponding fluid containers, the system 100 may include an anticoagulant pole 150 on which the anticoagulant solution container 210 (FIG. 3) may be hung, and a saline pole 160 on which a saline solution container 217 (FIG. 3) may be hung (e.g., if the procedure being performed requires the use of saline). Additionally, in some applications, it may be necessary and/or desirable to filter the whole blood drawn from the subject for processing. To that end, the system 100 may include blood filter holder 170 in which the blood filter (located on the disposable set) may be placed.

As discussed in greater detail below, apheresis systems 100 in accordance with embodiments of the present invention withdraw whole blood from a subject through a venous access device 206 (FIG. 3) using the blood pump 232. As the system 100 withdraws the whole blood from the subject, the whole blood enters a blood component separation device 214, such as a Latham type centrifuge (other type of separation chambers and devices may be used, such as, without limitation, an integral blow-molded centrifuge bowl, as described in U.S. Pat. Nos. 4,983,158 and 4,943, 273, which are hereby incorporated by reference). The blood component separation device 214 separates the whole blood into its constituent components (e.g., red blood cells, white blood cell, plasma, and platelets). Accordingly, to facilitate operation of the separation device 214, the system 100 may also include a well 180 in which the separation device 214 may be placed and in which the separation device 214 rotates (e.g., to generate the centrifugal forces required to separate the whole blood).

To allow the user/technician to monitor the system operation and control/set the various parameters of the procedure, the system 100 may include a user interface 190 (e.g., a touch screen device) that displays the operation parameters, any alarm messages, and buttons which the user/technician may depress to control the various parameters. Additional components of the blood processing system 100 are discussed in greater detail below (e.g., in relation to the system operation).

FIG. 3 is a schematic block diagram of the blood processing system 100 and a disposable collection set 200 (with an inlet disposable set 200A and an outlet disposable set 200B) that may be loaded onto/into the blood processing system 100, in accordance with the present invention. The collection set 200 includes a venous access device 206 (e.g., a phlebotomy needle) for withdrawing blood from a donor's arm 208, a container of anti-coagulant 210, a centrifugation bowl 214 (e.g., a blood component separation device), a saline container 217, and a final plasma collection bag 216. The blood/inlet line 218 couples the venous access device 206 to an inlet port 220 of the bowl 214, the plasma/outlet line 222 couples an outlet port 224 of the bowl 214 to the plasma collection bag 216, and a saline line 223 connects the outlet port 224 of the bowl 214 to the saline container 217. An anticoagulant line 225 connects the anti-coagulant container 210 to the inlet line 218. In addition to the components mentioned above and as shown in FIG. 3, the blood processing system 100 includes a controller 226, a motor 228, and a centrifuge chuck 230. The controller 226 is operably coupled to the two pumps 232 and 234, and to the motor 228, which, in turn, drives the chuck 230. The controller 226 may be operably coupled to and in communication with the user interface 190.

In operation, the disposable collection set 200 (e.g., the inlet disposable set 200A and the outlet disposable set 200B) may be loaded onto/into the blood processing system 100 prior to blood processing. In particular, the blood/inlet line 218 is routed through the blood/first pump 232 and the anticoagulant line 225 from the anti-coagulant container 210 is routed through the anticoagulant/second pump 234. The centrifugation bowl 214 may then be securely loaded into the chuck 230. Once the bowl 214 is secured in place, the technician may install the outlet disposable set 200B. For example the technician may connect a bowl connector 300 to the outlet 224 of the bowl 214, install the plasma container 216 into the weight senor 195, run the saline line 223 through valve 135, and run the plasma/outlet line 222 through valve 130 and the line sensor 185. Once the disposable set 200 is installed and the anticoagulant and saline containers 210/217 are connected, the system 100 is ready to begin blood processing.

Figure 4:
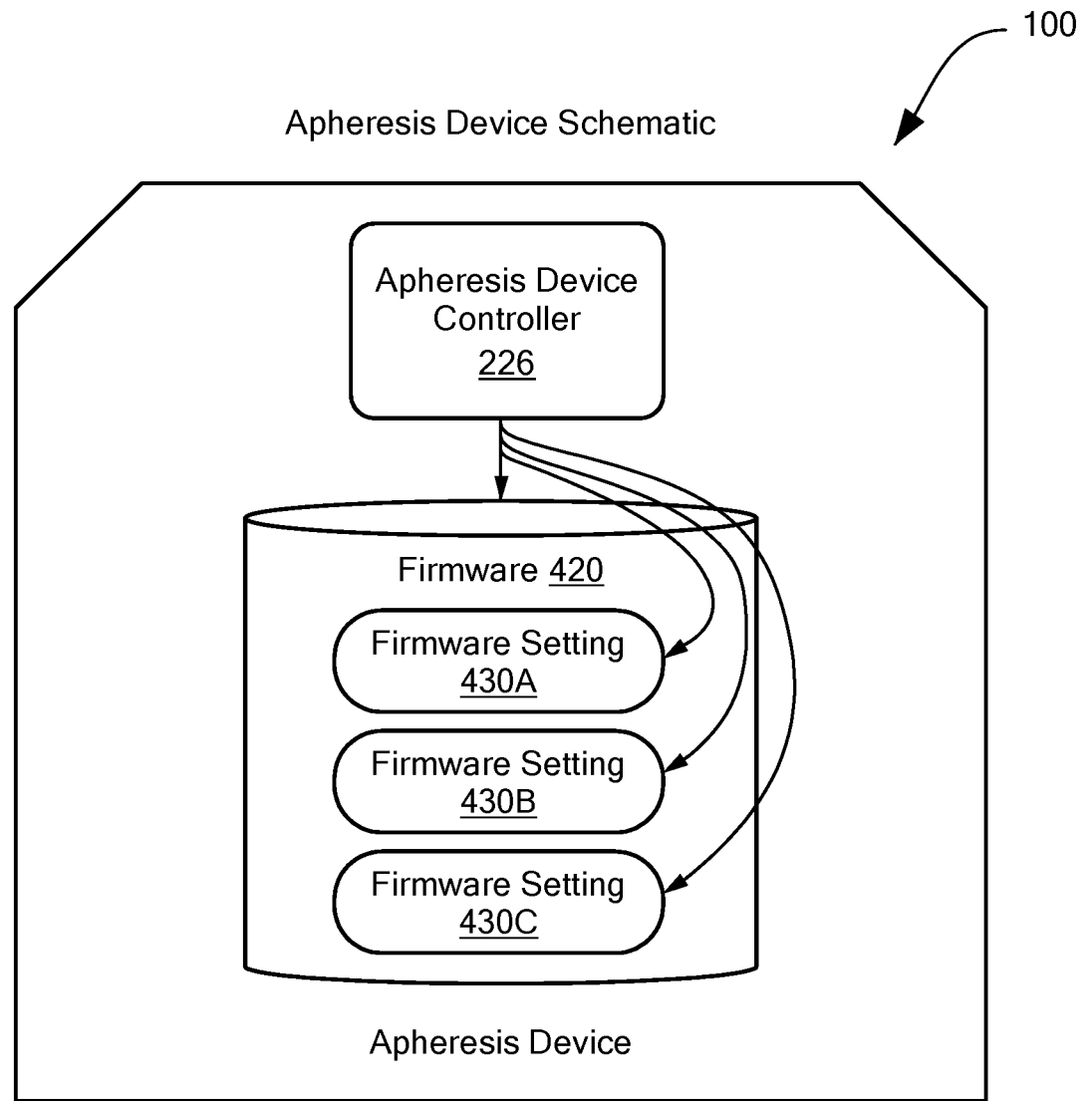
FIG. 4 schematically shows an apheresis device and its related firmware and firmware setting, in accordance with some embodiments of the present invention.

The blood processing system 100 (e.g., the apheresis device) and/or the individual hardware components of the blood processing system 100 may include firmware 420 and firmware settings 430A-C that control the various components of the blood processing system 100 (see FIG. 4) and the operation of the system 100. At various times, the firmware 420 and/or the firmware settings 430A/B/C may become outdated or otherwise need to be updated. To that end, the controller 226, along with the device's 100 input devices and display 190, may allow the user to access the device 100, for example, to review and/or update the firmware 420 and/or firmware settings 430A/B/C.

FIG. 5 schematically shows a fleet management system that may remotely update the firmware 420 and/or firmware settings 430A/B/C for one or more blood processing systems/apheresis devices 100. For example, the fleet management system 510 may be a remote computer system that oversees and manages some or all of apheresis devices 520A-F in a company's fleet. The management system 510 may include a number of components that helps the system 510 monitor, communicate with and update the firmware of the various apheresis devices. For example, the management system/device 510 may include a processor 530 that monitors each of apheresis device(s) 520A-F and the status of the firmware (e.g., the settings, the version, etc.), and a memory 540 (e.g., a data storage device) for storing information relating the apheresis device(s) 520A-F (e.g., the firmware version of each device, the firmware settings, dates of last updates, any issues with the firmware and/or firmware settings, etc.). Additionally, the system 510 may include a server 550 that communicates with the apheresis devices 520A-F (and, perhaps, other remote devices/systems) and a controller interface/display 560 that provides information to the user/operator.

As shown in FIG. 5, the apheresis devices 520A-F may be located in a single donation center 530A or in multiple donation centers 530A/B. The fleet management system 510 allows a user to remotely manage the apheresis device firmware files 420, firmware settings 430A-C, and perform various inspections of the firmware settings for each of the apheresis devices 520A-F. For example and as discussed in greater detail below, the server 550 may communicate with each of the apheresis devices 520A-F to monitor and download data regarding the firmware and firmware settings of each of the devices 520A-F. The processor 530 (or the server 550) may then process the received information/data to determine whether or not each device 520A-F requires an update to the firmware 420 and/or the firmware settings 430A-C.

It is important to note that because the fleet management system 510 allows the user to remotely manage each of the apheresis devices 520A-F, the user does not need to be physically present at each device 520A-F to manipulate the built in controls on each apheresis device (e.g., the user does not need to physically interact with each device's controller 226). The connectivity/communication between the fleet management system 510 and each of the apheresis devices 520A-F may be persistent/continuous or the fleet management system 510 may only be connected to the apheresis device 520A-F when needed (e.g., when the user wishes to monitor or manage the particular device). For example, the fleet management system 510 may continuously receive information/data related to the firmware of each apheresis device 520A-F (along with other information regarding the devices 520A-F), or the fleet management system 510 may only periodically receive the firmware information/data (e.g., at a predetermined interval, when prompted by a user, only when there is an update to distribute, only when prompted by the server 550 or system 510, etc.)

As noted above, the fleet management system 510 may manage a number apheresis devices 520A-F as needed. To that end, the fleet management system 510 (e.g., the server 550) may receive a firmware file from the user or from an external repository (or other remote device/database). If the system 510 has not already received the firmware information/data from each of the devices 520A-F (e.g., via the continuous connection or a recent periodic connection/ update), the server 550 may then connect to each of the devices 520A-F and download the firmware information/ data (including the current firmware version, firmware settings, and any firmware issues) for each of the devices 520A-F. Upon receipt of this information, the processor 530 may then determine which of the devices 520A-F require an update to the firmware 420 and/or the firmware settings 430A-C, and the system 510 (e.g., the server 550) may distribute the firmware file(s) to any of the device 520A-F that require the new firmware file(s) for installation.

In addition to sending the update/new firmware file(s) to each of the devices 520A-F that require it, the system 510 may also monitor the progress of the installation and/or firmware update and provide an alert to the user when the firmware file has been installed successfully and/or if the installation was unsuccessful. If the installation is unsuccessful, the system 100 may provide the user with an option to retry the download and installation. Additionally or alternatively, the fleet management system 510 may allow the user to manually inspect the firmware version of each of the apheresis devices 520A-F to confirm whether or not the firmware file has been installed successfully or unsuccessfully. For example, the system 510 may display (on the interface/display 560) each of the devices 520A-F for which the system 510 is connected/maintaining and, perhaps, the current firmware information of each device 520A-F. The user may then select the device 520A-F of interest for additional information regarding the device including, but not limited to, the location of the device, the service and use history of the device, the firmware 420 and firmware settings 430A-C information, the date of the last update, any recent error messages and/or the progress of any ongoing installations. It should be noted that the system 510 can display the devices 520A-F in any number of ways including, but not limited to, a list of devices or a floor plan of each plasma center 530A/B with an icon depicting each device 520A-F in the appropriate location.

In some embodiments, the user may not wish to update the firmware 420 and/or firmware settings 430A-C while the apheresis device 520A-F is in use. Therefore, any updates may be performed after regular donation hours at the plasma centers 530A/B. Alternatively, the system 510 (e.g., the server 550) may receive information regarding the operation status of each device 520A-F (e.g., whether it is in use) and/or whether the device 520A-F is scheduled to be used for an apheresis procedure. The management system 510 may then, based on this operational information, decide whether or not to update the firmware 420 and/or firmware settings 430A-C. For example, if the apheresis device 520A-F is in the middle of a procedure or is about to be used for a procedure, the system 510 may wait to distribute the firmware update to that device 520A-F. In a similar manner, the system 510 may notify the plasma centers 530A/B when a given device 520A-F is scheduled for an update to ensure that the device 520A-F is not assigned to a procedure until the update is complete.

At various times, the plasma centers 530A/530B may receive new apheresis devices 520A-F and/or replace existing devices 520A-F and these new devices may need initial configuration so that their firmware and firmware settings match the other devices within the centers 530A/B. To that end, the system 510 may configure these new devices (and/or configure/reconfigure existing devices 520A-F). In a similar manner to that described above, the system 510 may receive a firmware setting file from the user, from an external repository, or from at least one apheresis device

520A-F, and the fleet management system 510 may use the firmware setting file to configure some or all of apheresis devices 520A-F in the company's fleet. For example, the system 510 may display the devices 520A-F that require configuration on the interface/display 560 and the user may select which of the devices 520A-F to configure (or the system 510 may automatically configure the devices without input from the user). The system 510 (e.g., the server 550) may then distribute the firmware setting file to the appropriate apheresis device(s) 520A-F so that each of the devices receiving the firmware setting file may apply the changes represented in the firmware setting file. Once again, the system 510 may alert the user when the firmware setting changes have been applied successfully and/or if the update was unsuccessful (e.g., an error occurred). Additionally or alternatively, as mentioned above, the user may also use the system 510 to manually inspect the firmware settings of the apheresis device(s) 520A-F to confirm if the firmware setting file changes were applied successfully or unsuccessfully.

In some instances, it is beneficial to ensure that each of the apheresis devices 520A-F within a fleet and/or within a plasma center 530A/B are all operating with the same firmware version 420 and firmware settings 430A-C. Accordingly, in addition to updating and sending firmware updates to each of the apheresis devices 520A-F, the fleet management system 510 may collect information about the firmware version 420 or the firmware setting values 430A-C from each of the devices 520A-F in the fleet. The system 510 (e.g., the processor 530) may then aggregate, combine, and/or analyze the data to determine if there are any differences in the firmware version 420 or firmware setting values 430A-C between the apheresis devices 520A-F within the fleet and/or within a particular plasma center 530A/B.

If there is a discrepancy between any of the firmware versions 420 and/or firmware settings 430A-C, the system 510 may notify a user. For example, the system 210 may create and send an e-mail notification to a user or display a notification on the interface 560 when it detects a firmware version or firmware setting discrepancy. The system 510 may then give the user the opportunity to correct the discrepancies by downloading/distributing the appropriate firmware version 420 and/or settings 430A-C to the appropriate apheresis devices 520A-F (or download/distribute a new firmware version and/or new firmware settings to all devices apheresis devices 520A-F). Alternatively, the system 510 may automatically distribute the firmware file or the firmware setting file to apheresis devices to correct the discrepancies.

Figure 6:
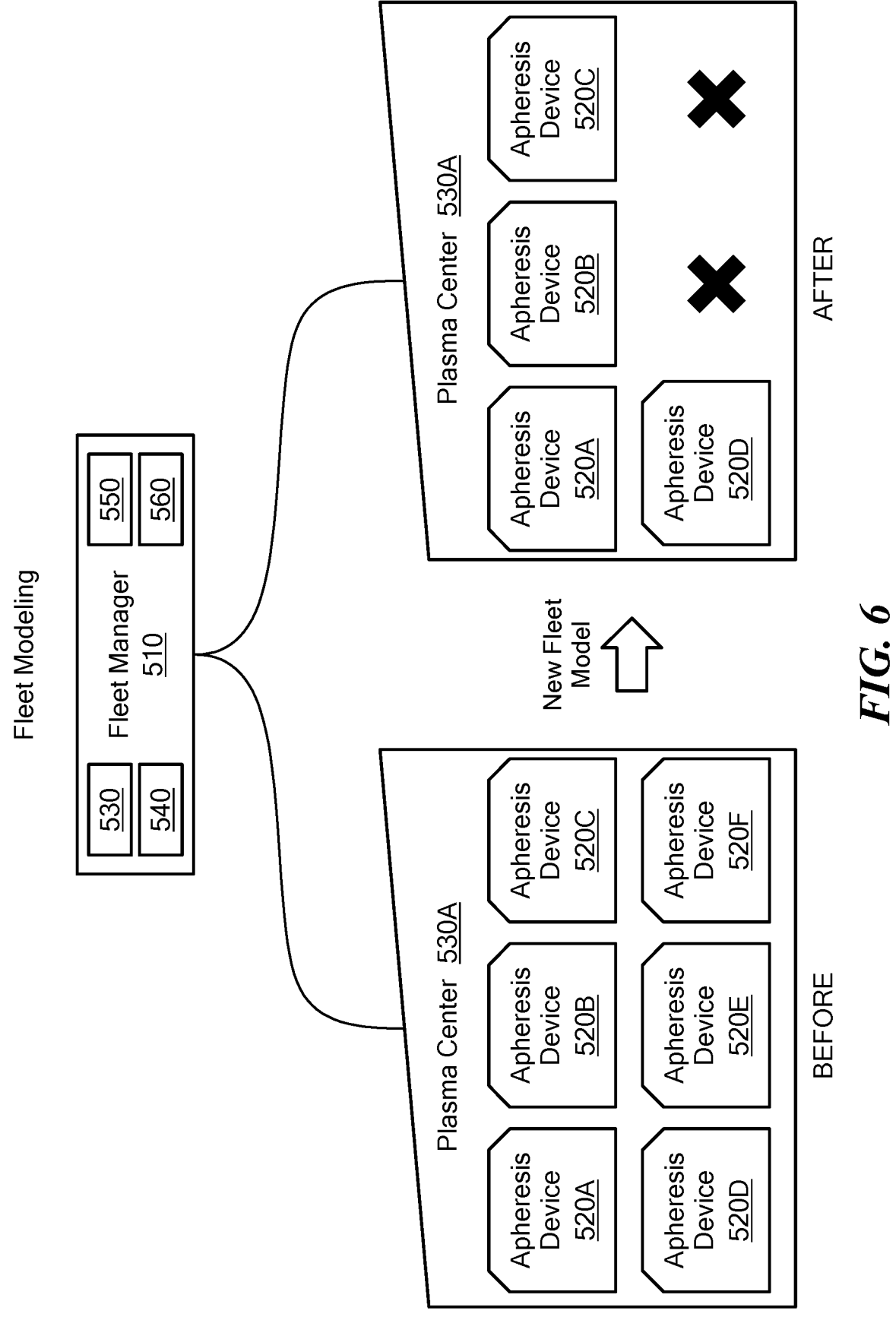
FIG. 6 schematically shows fleet management modeling to determine the optimal quantity and placement of apheresis devices at a plasma center location, in accordance with some embodiments of the present invention.

When planning out the type and number of apheresis devices 520A-F, the various plasma centers 530A/B must take into account a number of factors (e.g., the geographic location, anticipated donor participation, cost of the apheresis devices 520A-F, the maintenance cost of the apheresis devices 520A-F, size of the plasma center 530A/B, the types of donations and apheresis procedures that will be performed at the donation center, desired collection volumes for a given time period, etc.) to ensure that they have enough apheresis devices 520A-F to service the number of expected donors and reach target collection volumes without having too many apheresis devices 520A-F not in use at any given time. Therefore, in addition to updating the firmware 420 and firmware settings 430A-C on the devices 520A-F, in some embodiments and as shown in FIG. 6, the fleet management system 510 may help the plasma centers 530A/B determine an optimal number of apheresis device 520A-F to meet their expected demand and achieve their target volumes without having an excess of apheresis devices 520A-F. For example, in such embodiments, the system 510 may also download/receive information from the plasma center 530A/B (and each of the apheresis devices 520A-F) regarding the apheresis procedures performed at the plasma center 530A/B, productivity information from the plasma center 530A/B and, perhaps, information regarding the donor traffic and plasma center 530A/B targets. The system 510 (e.g., the processor 530) may then process and analyze the information data, for example, using heuristics based on the location of apheresis devices in the fleet and the productivity information from those locations to create a fleet model for the plasma center 530A.

The fleet model determines the optimal number of apheresis devices 520A-F for a location's profile and the system 510 may provide a directive for the user to either add or remove devices from the location based on the fleet model. For example, if the fleet model indicates that the plasma center 530A/B does not have a sufficient number of apheresis devices 520A-F to meet the demand/number of donors and/or reach the target collection volumes for the center 530A/B, the system 510 will notify the user that the plasma center 530A/B should add additional apheresis devices 520A-F. Alternatively, as shown in FIG. 6, if the fleet model determines that plasma center 530A/B has too many apheresis devices 520A-F, the system 510 may instruct the user to remove one or more of the apheresis devices 520A-F (e.g., to remove apheresis device 520E and 520F).

When generating the optimal fleet model for one or more locations, the system 510 may use variety of information including, but not limited to, productivity, utilization, telemetry, inventory, quantity, consumption, cost, timing, average, rate, speed data and/or other performance or production data of the same. The system 510 may also use apheresis device location data to determine plasma center locations that may require changes to device placement to meet the requirements of the new fleet model. Once the new fleet model is generated, the system 510 may provide a directive to the user in the form of digital assistance with instructions to adjust the placement of apheresis devices 520A-F at specific plasma center locations 530A/B in the company. For example, if the system 510 determines that plasma center 530A has too many apheresis devices 520A-F but plasma center 530B does not have enough, the system 510 may instruct the user to move/relocate one or more machines from plasma center 530A to plasma center 530B.

Although in many instances firmware 420 and firmware settings 430A-C becoming outdated may be anticipated (e.g., if a firmware update is released), in other cases the firmware 420 and firmware settings 430A-C may unexpectedly become corrupted and/or mutate. To that end, the system 510 may use the connectivity to the apheresis devices 520A-F in the fleet to monitor for firmware version differences or firmware settings differences. The system 510 may then track, log, and report (e.g., to the company or user) any unanticipated differences/mutations amongst apheresis devices 520A-F. The system 510 may maintain a history/record of the differences/mutations (and any other information received form the apheresis devices 520A-F or generated by the system 510) in the data storage device 440

It should be noted that, although the embodiments described above relate to plasma collection devices and plasma devices, various embodiments of the present invention may be used for other fleets of devices. For example, various embodiments of the present invention may be used for other types of donation centers (e.g., whole blood donation centers, platelet donation centers, etc.) and other types of apheresis devices. Furthermore, embodiments of the present invention can be used for other healthcare institutions and non-healthcare institutions.

It should be also noted that terms such as "controller," "processor" and "server" may be used herein to describe devices that may be used in certain embodiments of the present invention and should not be construed to limit the present invention to any particular device type or system unless the context otherwise requires. Thus, a system may include, without limitation, a client, server, computer, appliance, or other type of device. Such devices typically include one or more network interfaces for communicating over a communication network and a processor (e.g., a microprocessor with memory and other peripherals and/or application-specific hardware) configured accordingly to perform device and/or system functions. Communication networks generally may include public and/or private networks; may include local-area, wide-area, metropolitan-area, storage, and/or other types of networks; and may employ communication technologies including, but in no way limited to, analog technologies, digital technologies, optical technologies, wireless technologies, networking technologies, and internetworking technologies The various components of the control program may be implemented individually or in combination. For example, each component may be implemented or a dedicated server or a set of servers configured in a distributed manner It should also be noted that devices may use communication protocols and messages (e.g., messages created, transmitted, received, stored, and/or processed by the system), and such messages may be conveyed by a communication network or medium. Unless the context otherwise requires, the present invention should not be construed as being limited to any particular communication message type, communication message format, or communication protocol. Thus, a communication message generally may include, without limitation, a frame, packet, datagram, user datagram, cell, or other type of communication message. Unless the context requires otherwise, references to specific communication protocols are exemplary, and it should be understood that alternative embodiments may, as appropriate, employ variations of such communication protocols (e.g., modifications or extensions of the protocol that may be made from time-to-time) or other protocols either known or developed in the future.

It should also be noted that logic flows may be described herein to demonstrate various aspects of the invention, and should not be construed to limit the present invention to any particular logic flow or logic implementation. The described logic may be partitioned into different logic blocks (e.g., programs, modules, interfaces, functions, or subroutines) without changing the overall results or otherwise departing from the true scope of the invention. Often times, logic elements may be added, modified, omitted, performed in a different order, or implemented using different logic constructs (e.g., logic gates, looping primitives, conditional logic, and other logic constructs) without changing the overall results or otherwise departing from the true scope of the invention.

The present invention may be embodied in many different forms, including, but in no way limited to, computer program logic for use with a processor (e.g., a microprocessor, microcontroller, digital signal processor, or general purpose computer), programmable logic for use with a programmable logic device (e.g., a Field Programmable Gate Array (FPGA) or other programmable logic device (PLD)), discrete components, integrated circuitry (e.g., an Application Specific Integrated Circuit (ASIC)), or any other means including any combination thereof. In some embodiments of the present invention, predominantly all of the described logic is implemented as a set of computer program instructions that is converted into a computer executable form, stored as such in a computer readable medium, and executed by a microprocessor under the control of an operating system.

Computer program logic implementing all or part of the functionality previously described herein may be embodied in various forms, including, but in no way limited to, a source code form, a computer executable form, and various intermediate forms (e.g., forms generated by an assembler, compiler, linker, or locator). Source code may include a series of computer program instructions implemented in any of various programming languages (e.g., an object code, an assembly language, or a high-level language such as FOR-TRAN, C, C++, JAVA, or HTML) for use with various operating systems or operating environments. The source code may define and use various data structures and communication messages. The source code may be in a computer executable form (e.g., via an interpreter), or the source code may be converted (e.g., via a translator, assembler, or compiler) into a computer executable form.

The computer program may be fixed in any form (e.g., source code form, computer executable form, or an intermediate form) either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), a PC card (e.g., PCMCIA card), or other memory device. The computer program may be fixed in any form in a signal that is transmittable to a computer using any of various communication technologies, including, but in no way limited to, analog technologies, digital technologies, optical technologies, wireless technologies, networking technologies, and internetworking technologies. The computer program may be distributed in any form as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web).

Hardware logic (including programmable logic for use with a programmable logic device) implementing all or part of the functionality previously described herein may be designed using traditional manual methods, or may be designed, captured, simulated, or documented electronically using various tools, such as Computer Aided Design (CAD), a hardware description language (e.g., VHDL or AHDL), or a PLD programming language (e.g., PALASM, ABEL, or CUPL).

Programmable logic may be fixed either permanently or transitorily in a tangible storage medium, such as a semiconductor memory device (e.g., a RAM, ROM, PROM, EEPROM, or Flash-Programmable RAM), a magnetic memory device (e.g., a diskette or fixed disk), an optical memory device (e.g., a CD-ROM), or other memory device. The programmable logic may be fixed in a signal that is transmittable to a computer using any of various communication technologies, including, but in no way limited to, analog technologies, digital technologies, optical technologies, wireless technologies (e.g., Bluetooth), networking technologies, and internetworking technologies. The programmable logic may be distributed as a removable storage medium with accompanying printed or electronic documentation (e.g., shrink wrapped software), preloaded with a computer system (e.g., on system ROM or fixed disk), or distributed from a server or electronic bulletin board over the communication system (e.g., the Internet or World Wide Web). In fact, some embodiments, may be implemented in a software-as-a-service model ("SAAS") or cloud computing model. Of course, some embodiments of the invention may be implemented as a combination of both software (e.g., a computer program product) and hardware. Still other embodiments of the invention are implemented as entirely hardware, or entirely software.

The embodiments of the invention described above are intended to be merely exemplary; numerous variations and modifications will be apparent to those skilled in the art. All such variations and modifications are intended to be within the scope of the present invention as defined in any appended claims.

What is claimed is:

1. A fleet management system comprising:
   a first plurality of apheresis device, each of the first plurality of apheresis devices having a controller, firmware and firmware settings;
   a fleet management device remotely located from and in communication with each of the first plurality of apheresis devices, the fleet management device including:
   an interface configured to allow a user to interact with the fleet management device;
   a server configured to continuously or periodically request and receive information regarding the firmware and firmware settings of each of the first plurality of apheresis devices over a network and configured to receive a firmware file from the user and/or a remote repository; and
   a processor configured to:
      monitor the first plurality of apheresis devices by processing the information regarding the firmware and firmware settings received from each of the first plurality of apheresis devices to determine which of the first plurality of apheresis devices requires an update to the firmware and/or firmware settings,
   wherein the server is configured to distribute the firmware file to each of the first plurality of apheresis devices that require the update, and
      compile or analyze the information regarding the firmware and firmware settings received from each of the first plurality of apheresis devices to identify discrepancies between the firmware and firmware settings of two or more of the first plurality of apheresis devices,
   wherein the fleet management device is configured to notify the user of any discrepancies and/or distribute the firmware file to at least one of the plurality of apheresis devices to correct the discrepancies between the firmware and firmware setting of the first plurality of apheresis devices and pre-emptively ensure that each of the first plurality of apheresis devices are operating with the same firmware and firmware settings and each of the first plurality of apheresis devices is operating properly.

2. A fleet management system according to claim 1, further comprising a second plurality of apheresis devices located remotely from the fleet management device and in communication with the fleet management device.

3. A fleet management system according to claim 2, wherein:

the server is further configured to receive information regarding the firmware and firmware settings of each of the second plurality of apheresis devices, and the processor is further configured to process the information received from each of the second plurality of apheresis devices to determine which of the second plurality of apheresis devices requires an update to the firmware and/or firmware settings, the server configured to distribute the firmware file to each of the second plurality of apheresis devices that require the update.

4. A fleet management system according to claim 2, wherein the first plurality of apheresis devices are located in a first donation center and the second plurality of apheresis devices are located in a second donation center.

5. A fleet management system according to claim 1, wherein the fleet management device is configured to allow a user to remotely manage and/or monitor the firmware files and/or firmware settings of each of the first plurality of apheresis devices.

6. A fleet management system according to claim 5, wherein the fleet management device is configured to alert a user if the firmware file and/or a firmware setting file is successfully or unsuccessfully installed on the at least one of the first plurality of apheresis devices.

7. A fleet management system according to claim 1, wherein the fleet management device is configured to collect additional information from each of the first plurality of apheresis devices.

8. A fleet management system according to claim 7, wherein the collected additional information includes information selected from the group consisting of the apheresis procedures performed, productivity information, utilization information, quantity of apheresis devices within a donation center, performance data, and inventory data.

9. A fleet management system according to claim 1, wherein the fleet management device is configured to generate a fleet model for one or more donation centers.

10. A fleet management system according to claim 9, wherein the fleet model is based, at least in part, upon information selected from the group consisting of productivity, utilization, telemetry, inventory, quantity, consumption, cost, timing, average, rate, speed data and other performance or production data of the same.

11. A fleet management system according to claim 9, wherein the fleet model includes recommended apheresis device quantities for one or more donation centers, the server configured to notify the user of the fleet model and recommended apheresis device quantities.

12. A fleet management system according to claim 1, wherein the fleet management device includes a data storage device configured to store information received from the first plurality of apheresis devices.

13. A fleet management device comprising:

an interface configured to allow a user to interact with the fleet management device;

a server in communication with a first plurality of apheresis device located remotely over a network from the fleet management device, the server configured to continuously or periodically request and receive information regarding the firmware and firmware settings of each of the first plurality of apheresis devices and configured to receive a firmware file from the user and/or a remote repository; and a processor configured to;

monitor the first plurality of apheresis devices by processing the information regarding the firmware and firmware settings received from each of the first plurality of apheresis devices to determine which of the first plurality of apheresis devices requires an update to the firmware and/or firmware settings, wherein the server is configured to distribute the firmware file to each of the first plurality of apheresis devices that require the update, and compile or analyze the information regarding the firmware and firmware settings received from each of the first plurality of apheresis devices to identify discrepancies between the firmware and firmware settings of two or more of the first plurality of apheresis devices, wherein the fleet management device is configured to notify the user of any discrepancies and/or distribute the firmware file to at least one of the plurality of apheresis devices to correct the discrepancies between the firmware and firmware settings of the first plurality of apheresis devices and pre-emptively ensure that each of the first plurality of apheresis devices are operating with the same firmware and firmware settings and each of the first plurality of apheresis devices is operating properly.

14. A fleet management device according to claim 13, wherein the server is also in communication with a second plurality of apheresis devices located remotely from the fleet management device.

15. A fleet management device according to claim 14, wherein:

the server is further configured to receive information regarding the firmware and firmware settings of each of the second plurality of apheresis devices, and the processor is further configured to process the information received from each of the second plurality of apheresis devices to determine which of the second plurality of apheresis devices requires an update to the firmware and/or firmware settings, the server configured to distribute the firmware file to each of the second plurality of apheresis devices that require the update.

16. A fleet management device according to claim 14, wherein the first plurality of apheresis devices are located in a first donation center and the second plurality of apheresis devices are located in a second donation center.

17. A fleet management device according to claim 13, wherein the fleet management device is configured to allow a user to remotely manage and/or monitor the firmware files and/or firmware settings of each of the first plurality of apheresis devices.

18. A fleet management device according to claim 17, wherein the server is configured to alert a user if the firmware file and/or a firmware setting file is successfully or unsuccessfully installed on the at least one of the first plurality of apheresis devices.

19. A fleet management device according to claim 13, wherein the server is configured to receive additional information from each of the first plurality of apheresis devices.

20. A fleet management device according to claim 19, wherein the additional information includes information selected from the group consisting of the apheresis procedures performed, productivity information, utilization information, quantity of apheresis devices within a donation center, performance data, and inventory data.

21. A fleet management device according to claim 13, wherein the server and/or the processor is configured to generate a fleet model for one or more donation centers.

22. A fleet management device according to claim 21, wherein the fleet model is based, at least in part, upon information selected from the group consisting of productivity, utilization, telemetry, inventory, quantity, consumption, cost, timing, average, rate, speed data and other performance or production data of the same.

23. A fleet management device according to claim 21, wherein the fleet model includes recommended apheresis device quantities for one or more donation centers, the server configured to notify the user of the fleet model and recommended apheresis device quantities.

24. A fleet management device according to claim 13, further comprising a data storage device configured to store information received from the first plurality of apheresis devices.

25. A method for managing a fleet of apheresis devices comprising:

continuously or periodically requesting and receiving, with a server of a fleet management device, information regarding the firmware and firmware settings of each of a first plurality of apheresis devices over a network, each of the plurality of apheresis devices having a controller, firmware and firmware settings;

receiving, in the server of the fleet management device, a firmware file from a user and/or a remote repository;

processing, in a processor of the fleet management device, the information received from each of the first plurality of apheresis devices to determine which of the first plurality of apheresis devices requires an update to the firmware and/or firmware settings;

distributing, using the server of the fleet management device, the firmware file to each of the first plurality of apheresis devices that require the update;

analyzing the information regarding the firmware and firmware settings received from each of the first plurality of apheresis devices to identify at least one discrepancy between the firmware and firmware settings of two or more of the first plurality of apheresis devices;

sending, in response to identifying the at least one discrepancy, a notification to the user and/or the firmware file to at least one of the plurality of apheresis devices to correct the discrepancies between the firmware and firmware settings of the first plurality of apheresis devices and pre-emptively ensure that each of the first plurality of apheresis devices are operating with the same firmware and firmware settings and each of the first plurality of apheresis devices is operating properly.

26. A method according to claim 25, further comprising connecting to a second plurality of apheresis devices located remotely from the fleet management device.

27. A method according to claim 26, further comprising:

receiving, in the server of the fleet management device, information regarding the firmware and firmware settings of each of the second plurality of apheresis devices;

processing, using the processor of the fleet management device, the information received from each of the second plurality of apheresis devices to determine which of the second plurality of apheresis devices requires an update to the firmware and/or firmware settings; and distributing, using the server of the fleet management device, the firmware file to each of the second plurality of apheresis devices that require the update.

28. A method according to claim 26, wherein the first plurality of apheresis devices are located in a first donation center and the second plurality of apheresis devices are located in a second donation center.

29. A method according to claim 25, further comprising:

managing, using the fleet management device, the firmware files and/or firmware settings of each of the first plurality of apheresis devices.

30. A method according to claim 29, further comprising:

generating an alert to a user if the firmware file and/or a firmware setting file is successfully or unsuccessfully installed on the at least one of the first plurality of apheresis devices.

31. A method according to claim 25, further comprising:

collecting additional information from each of the first plurality of apheresis devices.

32. A method according to claim 31, wherein the collected additional information includes information selected from the group consisting of the apheresis procedures performed, productivity information, utilization information, quantity of apheresis devices within a donation center, performance data, and inventory data.

33. A method according to claim 25, further comprising generating a fleet model for one or more donation centers.

34. A method according to claim 33, wherein the fleet model is based, at least in part, upon information selected from the group consisting of productivity, utilization, telemetry, inventory, quantity, consumption, cost, timing, average, rate, speed data and other performance or production data of the same.

35. A method according to claim 33, wherein the fleet model includes recommended apheresis device quantities for one or more donation centers, the method further comprising notifying the user of the fleet model and recommended apheresis device quantities.

36. A method according to claim 25, further comprising:

storing, in a data storage device in the fleet management device, information received from the first plurality of apheresis devices.

\* \* \* \* \*